United States Patent [19]

Bordier et al.

[11] Patent Number: 5,679,829

[45] Date of Patent: Oct. 21, 1997

[54] ARGININE DERIVATIVES, PROCESS OF PREPARATION, USES, AND COMPOSITIONS COMPRISING THEM

[75] Inventors: Thierry Bordier, Tremblay En France; Michel Philippe, Wissous; Sylvie Genard, Paris, all of France

[73] Assignee: L'Oreal, Paris, France

[21] Appl. No.: 590,445

[22] Filed: Jan. 23, 1996

[30] Foreign Application Priority Data

Jan. 31, 1995 [FR] France ................ 95 01114

[51] Int. Cl.$^6$ ................ C07C 261/00
[52] U.S. Cl. ................ 560/159; 424/401
[58] Field of Search ................ 560/159; 424/401

[56] References Cited

U.S. PATENT DOCUMENTS

| | | |
|---|---|---|
| 3,856,848 | 12/1974 | Smithwick . |
| 4,447,429 | 5/1984 | Silbering et al. . |
| 4,859,653 | 8/1989 | Morelle ................ 514/2 |
| 5,082,866 | 1/1992 | Wong ................ 514/785 |
| 5,587,169 | 12/1996 | Philippe ................ 424/401 |

FOREIGN PATENT DOCUMENTS

| | | |
|---|---|---|
| A0139481 | 9/1984 | European Pat. Off. . |
| A0336265 | 3/1989 | European Pat. Off. . |
| 766678 | 10/1970 | Germany ................ 560/169 |

*Primary Examiner*—Michael L. Shippen
*Attorney, Agent, or Firm*—Finnegan, Henderson, Farabow, Garrett & Dunner, L.L.P.

[57] ABSTRACT

New arginine derivatives containing an $N^\alpha$-alkyloxycarbonyl group of formula (I)

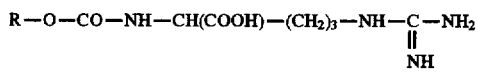

in which R represents a linear or branched alkyl radical having from 8 to 22 carbon atoms, salts thereof, and mixtures of the derivatives and the salts.

A process for the preparation of these derivatives, salts, and mixtures and use of such derivatives, salts, and mixtures, especially in cosmetics. Compositions, especially cosmetic compositions, comprising the derivatives, salts, and mixtures.

35 Claims, No Drawings

ARGININE DERIVATIVES, PROCESS OF PREPARATION, USES, AND COMPOSITIONS COMPRISING THEM

The subject of the present invention is compounds containing an $N^\alpha$-alkyloxycarbonyl group, which are derived from arginine, their process of preparation, their use, especially in cosmetics, and the compositions, especially cosmetic compositions, comprising them.

Compositions, especially cosmetic, pharmaceutical or food compositions, are known which can be presented in the form of a powder, known as a compact powder, obtained by compacting. They are generally anhydrous compositions which may mainly be composed of solid particles and of a fatty binder, shaped by compression.

The development of such compositions raises, however, many difficulties because the final composition must be sufficiently homogeneous and compact to have a good ability to be removed and, moreover, to avoid fragmentation which may be caused, especially, by impacts.

A description is given, in Patent Application EP 139,481, of cosmetic compositions using, as agents for modifying the surface of inorganic compounds, for the purpose of increasing the dispersibility thereof, either a monoacylated derivative of a basic amino acid in which the aliphatic acyl group has 8–22 carbon atoms or an N,N-diacylated derivative of a basic amino acid in which the acyl groups, which are identical or different, have 1–22 carbon atoms.

A description is also given, in Patent Application EP 336,265, of cosmetic compositions for hair shaping comprising, as surface-active agents, an N-monoacylated derivative of a basic amino acid in which the acyl group has 8–22 carbon atoms.

However, it is observed that the acylated derivatives of the basic amino acids described previously are very difficult and even impossible to compact.

The aim of the present invention is to provide new compounds which make it possible to facilitate the preparation of such compositions, whilst satisfying the above-mentioned requirements, without exhibiting the disadvantages of the prior art.

The subject of the present invention is therefore an arginine derivative containing $N^\alpha$-alkyloxycarbonyl groups of formula (I)

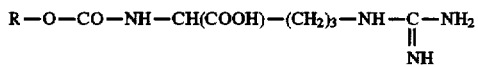

in which R represents a linear or branched saturated alkyl radical having from 8 to 22 carbon atoms,
the salts of the compounds of formula (I), their optical isomers of D or L configuration, and their mixtures.

Another subject of the invention is a composition, inter alia, cosmetic, pharmaceutical, hygiene or food, comprising at least one derivative of formula (I).

A further subject of the invention is the use of at least one derivative of formula (I) as a substance for coating substrate particles. It has in fact been observed that the said particles, generally powders, when they were coated by the derivative according to the invention, make it possible to obtain, after compacting, a good cohesion of the product, that is to say that the compacted product does not easily disintegrate.

Moreover, it has been observed that the derivatives according to the invention also make it possible to confer particularly advantageous spreading and skin-adhesion qualities, as well as a pleasant and smooth feel, on the cosmetic composition comprising them.

More precisely, the subject of the invention is an arginine derivative of formula (I):

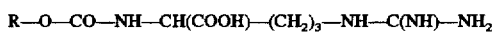

in which R preferably represents a linear or branched saturated alkyl radical having from 8 to 22 carbon atoms, the salts of the compounds of formula (I), their optical isomers of D or L configuration, and their mixtures.

The R radical can preferably represent a linear or branched alkyl radical having from 8 to 16 carbon atoms.

Mention may be made, among the derivatives according to the invention, of $N^\alpha$-dodecyloxycarbonyl-L-arginine, $N^\alpha$-2-ethylhexyloxycarbonyl-L-arginine, $N^\alpha$-decyloxycarbonyl-L-arginine and $N^\alpha$-hexadecyloxycarbonyl-L-arginine.

The salts of the derivatives according to the invention can be chosen from the salts of monovalent inorganic cations, such as those of sodium, or of divalent inorganic cations, such as those of zinc or copper.

The salts of the derivatives can also be chosen from the salts of organic cations, such as those of aminopropanediol, tris-hydroxyaminomethane, glucamine and N-methylglucamine.

The derivatives according to the invention can be provided in a solid form having a particle size generally ranging from 10 to 500,000 nm and preferably ranging from 100 to 25,000 nm.

The derivatives according to the invention are generally insoluble in oils and in aqueous solutions in which the pH ranges from 5 to 8.

The derivatives according to the invention generally have a high melting point, greater than 120° C.

The composition according to the invention comprising the said derivatives can be provided in various forms such as dispersions, optionally thickened or gelled lotions, optionally "compacted" powders, milks, creams, sticks, foams or sprays when it is packaged as an aerosol, oil-in-water or water-in-oil emulsions, liposomal dispersions or alternatively solid preparations.

The derivatives according to the invention can be included in the composition in a proportion generally ranging from 0.05% to 80% by weight, preferably in a proportion from 0.5 to 30% by weight, with respect to the total weight of the composition.

The derivatives according to the invention can be present in the composition in the free form and/or in the form of a combination with substrate particles which they coat.

In addition to the derivative according to the invention, the composition can also comprise at least one additive chosen from the group consisting of surface-active agents, fatty substances, inorganic solvents, silicones, thickeners, emollients, sunscreen agents, treating agents, anti-foaming agents, moisturizing agents, fragrances, preservatives, anti-oxidising agents, sequestrants, flavouring agents, basifying or acidifying agents, fillers and pigments.

Mention may be made, among the fatty substances which can be used in the composition according to the invention, of oils, waxes, fatty acids, fatty alcohols and/or their mixture.

The oils and the waxes can be of animal, vegetable, inorganic or synthetic origin. Mention may be made, among the oils, of hydrogenated palm oil, hydrogenated castor oil, liquid petrolatum, liquid paraffin or purcellin oil.

Mention may be made, among the waxes, of beeswax, montan wax, carnauba wax, candelilla wax, sugar cane wax, Japan wax, ozocerite, microcrystalline waxes, paraffin wax, lanolin wax, hydrogenated lanolin wax and acetylated lanolin wax.

Mention may especially be made, among the particles which can be coated by the derivatives according to the invention, of pigments, particulate fillers and microspheres such as hollow vinylidene chloride/acrylonitrile copolymer microspheres.

Mention may more particularly be made, among the fillers, of optionally coloured insoluble fillers such as nanopigments of metal oxides, such as titanium, zinc, iron, manganese, caesium and/or zirconium oxides.

The composition according to the invention can be provided in the form of make-up compositions such as foundation creams, tinted creams, mascaras, blushers, eye shadows, lipsticks and nail varnishes.

According to a specific embodiment, it can be provided in the so-called compact form, the derivative according to the invention facilitating compaction of the ingredients of the said compositions. Mention may especially be made, among these compact compositions, of foundation creams, blushers, eyeshadows and lipsticks.

The composition according to the invention can also be provided in the form of a pharmaceutical or hygiene composition, such as toothpastes, exfoliative compositions, powders for the body or for babies, and anti-perspirant powders, or indeed in the form of a food composition.

Another subject of the invention is a process for the preparation of the derivative of formula (I), consisting:

reacting, in aqueous medium and at basic pH, arginine, at least one its salts, or a mixture of arginine and at least one of its salts, of known configuration, with a compound of formula R—O—CO—X, in which R represents a linear or branched saturated alkyl radical having from 8 to 22 carbon atoms and X is chosen from the group consisting of a chlorine atom, a chloromethyl radical and an imidazolyl radical, and then, optionally purifying the arginine derivative, the salt, or the mixture obtained.

The compound of formula R—O—CO—X can be added without solvent.

The basic pH of the reaction mixture is preferably between 8 and 14.

Examples of the preparation of arginine derivatives according to the invention, and an example of a composition comprising such a derivative, will now be given by way of illustration only and do not limit the invention in any way.

EXAMPLE 1: PREPARATION OF N$^\alpha$-DODECYLOXYCARBONYL-L-ARGININE 10 g of L-arginine are dissolved in 100 ml of water in a 500 ml three-necked, round-bottomed flask, and then 50 ml of THF are added.

14.3 g of dodecyl chloroformate are added dropwise to the L-arginine solution while the apparent pH is kept constant by the addition of sodium hydroxide. After stirring vigorously for 16 hours, the reaction mixture is cooled to 0° C. and 400 ml of ice-cold acetone are added. The precipitate obtained is filtered off on sintered glass, washed and dried under reduced pressure before being recrystallized from absolute ethanol.

12.6 g (57% yield) of product are obtained.

Chemical analysis gives the following characteristics: Melting: T>140° C. (Kofler stage) Molecular weight: 386.539 Elemental analysis: $C_{19}H_{38}N_4O_4$

|  | C | H | N | O |
|---|---|---|---|---|
| % calculated | 59.04 | 9.91 | 14.49 | 16.56 |
| % measured | 58.57 | 10.00 | 14.32 | 16.96 |

$^1$H NMR: at 400 MHz in $d_6$-DMSO: 0.86 (t, 3 H), 1.43 and 1.45 to 1.63 (m, 24 H), 3.03 (t, 2 H), 3.67 (m, 1 H), 3.90 (t, 2 H), 6.2 (m, 1 H), 7.9 (m, 5 H).

EXAMPLE 2: PREPARATION OF N$^\alpha$-ETHYLHEXYLOXYCARBONYL-L-ARGININE 10 g of L-arginine are dissolved in 100 ml of water in a 500 ml three-necked, round-bottomed flask and then 50 ml of THF are added.

11.05 g of 2-ethylhexyl chloroformate are added dropwise to the L-arginine solution while the apparent pH is kept constant by the addition of sodium hydroxide. After stirring vigorously for 16 hours, the reaction mixture is cooled to 0° C. and 100 ml of ice-cold acetone are added. The residual arginine is separated by filtering on sintered glass, while the filtrate is concentrated under reduced pressure in the presence of isopropanol. The residue is purified several times by dissolving in the minimum amount of water followed by precipitating the salts with isopropanol, filtering and concentrating the filtrate.

18.8 g (yield in the region of 99%) of product are obtained in the form of a pulverulent solid.

Chemical analysis gives the following characteristics: Melting: T>120° C. Molecular weight: 330.431 Elemental analysis: $C_{15}H_{30}N_4O_4 \cdot H_2O$

|  | C | H | N | O |
|---|---|---|---|---|
| % calculated | 51.70 | 9.26 | 16.07 | 22.96 |
| % measured | 51.12 | 8.68 | 16.07 | 21.62 |

$^1$H NMR at 400 MHz in $d_6$-DMSO ($\delta$ in ppm): 0.85 (t, 3 H), 0.87 (t, 3 H), 1.27 to 1.66 (m, 13 H), 3.05 (t, 2 H), 3.67 (m, 1 H), 3.84 (m, 2 H), 6.2 (m, 1 H), 7.6 (m, 4 H), 9.1 (m, 1 H).

EXAMPLE 3: PREPARATION OF N$^\alpha$-DECYLOXYCARBONYL-L-ARGININE 10 g of L-arginine are dissolved in 100 ml of water in a 250 ml three-necked, round-bottomed flask and then 50 ml of THF are added.

12.6 g of decyl chloroformate are added dropwise to the L-arginine solution while the apparent pH is kept constant by the addition of sodium hydroxide. After stirring vigorously for 16 hours, the heterogeneous reaction mixture is cooled to 5° C., 200 ml of ice-cold acetone are added and the reaction mixture is then filtered on sintered glass. The precipitate is washed several times with acetone, dried and recrystallized from a ⅔ acetone/methanol mixture with hot filtration and then washing with acetone and drying.

9.2 g (44% yield) of product are obtained.

Chemical analysis gives the following characteristics: Melting: T>134° C. Molecular weight: 358.485 Elemental analysis: $C_{17}H_{34}N_4O_4$

| | C | H | N | O |
|---|---|---|---|---|
| % calculated | 56.98 | 9.49 | 15.64 | 17.88 |
| % measured | 56.89 | 9.50 | 15.73 | 17.69 |

$^1$H NMR at 250 MHz in $d_6$-DMSO (δ in ppm): 0.86 (t, 3 H), 1.25 to 1.64 (m, 20 H), 3.02 (m, 2 H), 3.65 (m, 1 H), 3.89 (t, 2 H), 6.35 (d, 1 H), 7.1 to 8.1 (m, 4 H), 9.33 (m, 1 H)

EXAMPLE 4: PREPARATION OF N$^\alpha$-HEXADECYLOXYCARBONYL-L-ARGININE 10 g of L-arginine are dissolved in 100 ml of water in a 250 ml three-necked, round-bottomed flask and then 50 ml of THF are added.

17.5 g of hexadecyl chloroformate are added dropwise to the L-arginine solution while the apparent pH is kept constant by the addition of sodium hydroxide. After stirring vigorously for 16 hours, the heterogeneous reaction mixture is cooled to 5° C., 1 liter of ice-cold acetone is added and the reaction mixture is then filtered on sintered glass. The precipitate is washed several times with acetone, dried and recrystallized from ethanol with hot filtration and then washing and drying.

14.75 g (58% yield) of product are obtained.

Chemical analysis gives the following characteristics: Melting: T>130° C. Molecular weight: 442.647 Elemental analysis: $C_{23}H_{46}N_4O_4 \cdot H_2O$

| | C | H | N | O |
|---|---|---|---|---|
| % calculated | 59.97 | 10.50 | 12.15 | 17.37 |
| % measured | 60.31–60.59 | 10.04–10.19 | 11.61 | 16.40–16.50 |

$^1$H NMR at 500 MHz in $d_6$-DMSO (δ in ppm): 0.86 (t, 3 H), 1.25 to 1.38 and 1.40 to 1.65 (m, 32 H), 3.03 (dd, 2 H), 3.66 (dd, 1 H), 3.88 (t, 2 H), 6.26 (d, 1 H), 7.2 to 8.0 (m, 4 H), 9.3 (m, 1 H)

EXAMPLE 5: PREPARATION OF A COMPACTED POWDER

A powder is prepared which has the following composition:

| Composition A: | |
|---|---|
| Talc | 38.4 g |
| Bismuth oxychloride | 10 g |
| Zinc stearate | 4 g |
| Compound of Example 4 | 20 g |
| Nylon powder | 20 g |

| Composition B: | |
|---|---|
| Iron oxides | 1.6 g |
| Liquid petrolatum | 6 g |

The powder is obtained in the following way: the composition A is ground in a grinder of Kenwood type for approximately 5 minutes with gentle agitation. The composition B is added and the combined mixture is ground for approximately 2 minutes at the same speed and then for 3 minutes at a faster speed. The preparation is then sieved on a 0.16 mm sieve and this mixture is then compacted in small dishes.

A compacted powder is obtained which has good adhesion and which spreads readily and pleasantly on the skin, while being smooth to the touch.

The presence of the compound of Example 4 prevents excessively easy disintegration of the compacted product.

We claim:

1. At least one arginine derivative comprising an N$^\alpha$-alkyloxycarbonyl group of formula (I)

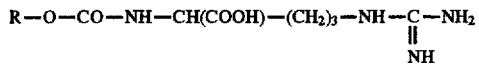

wherein R represents a linear or branched saturated alkyl radical having from 8 to 22 carbon atoms, at least one salt of the arginine derivative of formula (I), or a mixture of at least one said arginine derivative of formula (I) and at least one said salt of the arginine derivative of formula (I).

2. At least one derivative or at least one salt according to claim 1, wherein said derivative or said salt is an optical isomer of D or L configuration.

3. At least one derivative or at least one salt according to claim 1, wherein R has from 8 to 16 carbon atoms.

4. At least one salt according to claim 1 wherein said salt is a salt of a monovalent inorganic cation, a divalent inorganic cation, or an organic cation.

5. At least one salt according to claim 4 wherein said monovalent inorganic cation is sodium.

6. At least one salt according to claim 4 wherein said divalent inorganic cation is zinc or copper.

7. At least one salt according to claim 4 wherein said organic cation is a cation of aminopropanediol, trishydroxyaminomethane, glucamine, or N-methylglucamine.

8. At least one derivative according to claim 1, wherein said derivative is N$^\alpha$-dodecyloxycarbonyl-L-arginine, N$^\alpha$-2-ethylhexyloxycarbonyl-L-arginine, N$^\alpha$-decyloxycarbonyl-L-arginine or N$^\alpha$-hexadecyloxycarbonyl-L-arginine.

9. At least one derivative or at least one salt according to claim 1 wherein said derivative or said salt has a particle size ranging from 10 nm to 500,000 nm.

10. At least one derivative or at least one salt according to claim 9 wherein said particle size ranges from 100 nm to 25,000 nm.

11. A composition comprising, according to claim 1, at least one derivative, at least one salt of said derivative, or a mixture of at least one said derivative and at least one said salt.

12. A composition according to claim 11, said composition being a dispersion, an optionally thickened or gelled lotion, an optionally compacted powder, a milk, a cream, a stick, a foam, a spray, an oil-in-water emulsion, a water-in-oil emulsion, or a liposomal dispersion.

13. A composition according to claim 11 wherein said derivative, said salt, or said mixture ranges from 0.05% to 80% by weight with respect to the total weight of the composition.

14. A composition according to claim 13 wherein said derivative, said salt, or said mixture ranges from 0.5% to 30% by weight with respect to the total weight of the composition.

15. A composition according to claim 11 wherein said derivative, said salt, or said mixture is in the free form, is in the form of a combination with substrate particles coated by said derivative, said salt, or said mixture, or is in the form of a mixture of said free form and said combination.

16. A composition according to claim 15 wherein said substrate particles are selected from pigments, particulate fillers and microspheres.

17. A composition according to claim 16 wherein said microspheres are hollow vinylidene chloride/acrylonitrile copolymer microspheres.

18. A composition according to claim 11 further comprising at least one additive selected from surface-active agents, fatty substances, organic solvents, silicones, thickeners, emollients, sunscreen agents, treating agents, anti-foaming agents, moisturizing agents, fragrances, preservatives, anti-oxidizing agents, sequestrants, flavouring agents, basifying and acidifying agents, fillers, and pigments.

19. A composition according to claim 18 wherein said fatty substances are selected from oils, waxes, fatty acids, and fatty alcohols.

20. A composition according to claim 19 wherein said oils are of animal, vegetable, inorganic, or synthetic origin.

21. A composition according to claim 20 wherein said oil is hydrogenated palm oil, hydrogenated castor oil, liquid petrolatum, liquid paraffin or purcellin oil.

22. A composition according to claim 19 wherein said waxes are of animal, vegetable, inorganic or synthetic origin.

23. A composition according to claim 22 wherein said wax is beeswax, montan wax, carnauba wax, candelilla wax, sugar cane wax, Japan wax, ozocerite, microcrystalline waxes, paraffin wax, lanolin wax, hydrogenated lanolin wax or acetylated lanolin wax.

24. A composition according to claim 16 wherein said particulate fillers are optionally coloured insoluble fillers.

25. A composition according to claim 24 wherein said optionally coloured insoluble fillers are selected from nanopigments of metal oxides.

26. A composition according to claim 25 wherein said nanopigments of metal oxides are selected from titanium, zinc, iron, manganese, caesium and zirconium oxides.

27. A composition according to claim 11 wherein said composition is in the form of a make-up composition.

28. A composition according to claim 27, said make-up composition being a foundation cream, a tinted cream, a mascara, a blusher, an eye shadow, a lipstick or a nail varnish.

29. A composition according to claim 27, said make-up composition being in the compact form.

30. A composition according to claim 29, said make-up composition being a foundation cream, a blusher, an eye shadow or a lipstick.

31. A composition according to claim 11, said composition being a a cosmetic composition, a pharmaceutical composition, a hygiene composition, or a food composition.

32. A composition according to claim 31, said composition being a toothpaste, an exfoliative composition, a skin-care composition, a body powder, or an anti-perspirant.

33. A process for the preparation of a derivative, salt, or mixture according to claim 1 comprising the steps of:

reacting arginine, at least one salt of arginine, or a mixture of arginine and at least one of said salts in an aqueous medium and at a basic pH, with a compound of formula

wherein R represents a linear or branched saturated alkyl radical having from 8 to 22 carbon atoms, and X is a chlorine atom, a chloromethyl radical or an imidazolyl radical; and optionally purifying the arginine derivative, the salt, or the mixture obtained.

34. A method of coating a substrate particle comprising the step of coating a substrate particle with said derivative, said salt, or said mixture according to claim 1.

35. A method for facilitating compaction of compositions including particles comprising the steps of including in a composition at least one derivative, at least one salt, or a mixture according to claim 1, either as particles or as a coating on substrate particles, said coated substrate particles being included in said composition; and thereafter compacting said composition.

* * * * *